(12) United States Patent
Jo et al.

(10) Patent No.: US 11,311,208 B2
(45) Date of Patent: Apr. 26, 2022

(54) HEALTH INFORMATION PROVIDING SYSTEM THROUGH PLANTAR PRESSURE MEASUREMENT

(71) Applicants: Byung Woo Jo, Busan (KR); Bo Soek Kim, Changwon-si (KR)

(72) Inventors: Byung Woo Jo, Busan (KR); Jae Han Park, Miryang-si (KR)

(73) Assignees: Byung Woo Jo, Busan (KR); Bo Soek Kim, Changwon-si (KR)

( * ) Notice: Subject to any disclaimer, the term of this patent is extended or adjusted under 35 U.S.C. 154(b) by 426 days.

(21) Appl. No.: 16/339,953

(22) PCT Filed: Oct. 10, 2017

(86) PCT No.: PCT/KR2017/011135
§ 371 (c)(1),
(2) Date: Apr. 5, 2019

(87) PCT Pub. No.: WO2018/066978
PCT Pub. Date: Apr. 12, 2018

(65) Prior Publication Data
US 2020/0046258 A1 Feb. 13, 2020

(30) Foreign Application Priority Data

Oct. 6, 2016 (KR) .................. 10-2016-0129157

(51) Int. Cl.
*A61B 5/103* (2006.01)
*G16H 70/60* (2018.01)
(Continued)

(52) U.S. Cl.
CPC .......... *A61B 5/1036* (2013.01); *A61B 5/0002* (2013.01); *A61B 5/486* (2013.01);
(Continued)

(58) Field of Classification Search
CPC ..... A61B 5/1036; A61B 5/0002; A61B 5/486; A61B 5/742; A61B 2560/0214;
(Continued)

(56) References Cited

U.S. PATENT DOCUMENTS

| 5,042,504 A | * | 8/1991 | Huberti | ............... A61B 5/1036 600/592 |
| 7,645,211 B1 | * | 1/2010 | Thomeczek | ....... A63B 69/0053 482/1 |
| 2010/0094174 A1 | * | 4/2010 | Choi | .................... A61B 5/1127 600/587 |

FOREIGN PATENT DOCUMENTS

| JP | 2013-192721 A | 9/2013 |
| KR | 20-0395775 Y1 | 9/2005 |

(Continued)

OTHER PUBLICATIONS

International Search Report for PCT/KR2017/011135 dated Feb. 1, 2018 from Korean Intellectual Property Office.

*Primary Examiner* — Patrick Fernandes
(74) *Attorney, Agent, or Firm* — Paratus Law Group, PLLC

(57) ABSTRACT

A health information providing system through plantar pressure measurement, including: a plantar pressure measurement device rolled in such a manner as to be carried and adapted to measure a measurement subject's plantar pressures in a state of being unrolled to transmit the measured plantar pressures to a measurement subject terminal; and the measurement subject terminal adapted to compare the plantar pressures received from the plantar pressure measurement device with reference plantar pressure ranges according to foot portions pre-stored, to extract and display a body region where a disease is suspected, the body region matching the foot portion having the plantar pressure exceeding the reference plantar pressure ranges according to foot (Continued)

portions, and to display health guidance information including guidance information on symptoms and treatments of the extracted body region where the disease is suspected.

6 Claims, 14 Drawing Sheets

(51) Int. Cl.
*G16H 40/63* (2018.01)
*G16H 70/20* (2018.01)
*A61B 5/00* (2006.01)

(52) U.S. Cl.
CPC .............. *A61B 5/742* (2013.01); *G16H 40/63* (2018.01); *G16H 70/20* (2018.01); *G16H 70/60* (2018.01); *A61B 2560/0214* (2013.01); *A61B 2562/0247* (2013.01); *A61B 2562/046* (2013.01)

(58) Field of Classification Search
CPC ...... A61B 2562/0247; A61B 2562/046; G16H 70/60; G16H 40/63; G16H 70/20
See application file for complete search history.

(56) References Cited

FOREIGN PATENT DOCUMENTS

| | | |
|---|---|---|
| KR | 10-0760048 B1 | 9/2007 |
| KR | 10-0909350 B1 | 7/2009 |
| KR | 10-2016-0042262 A | 4/2016 |
| KR | 10-2016-0065734 A | 6/2016 |

\* cited by examiner

【FIG. 1】
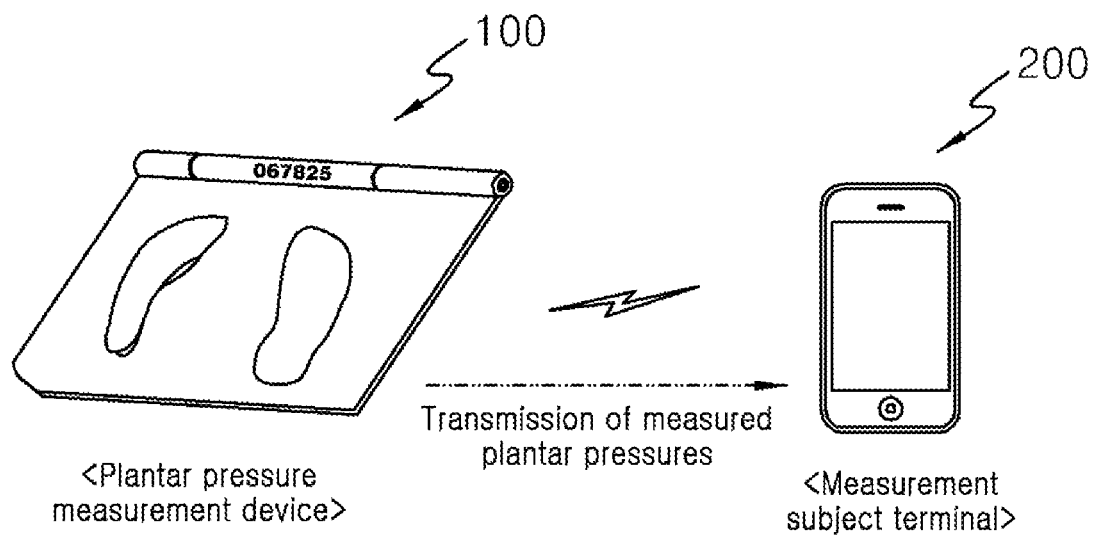
<Plantar pressure measurement device>
Transmission of measured plantar pressures
<Measurement subject terminal>
【FIG. 2】
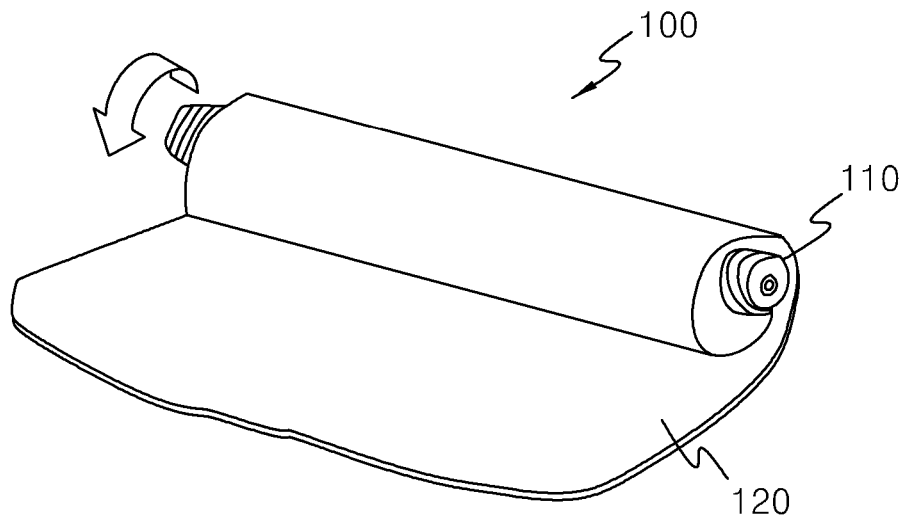

【FIG. 3】
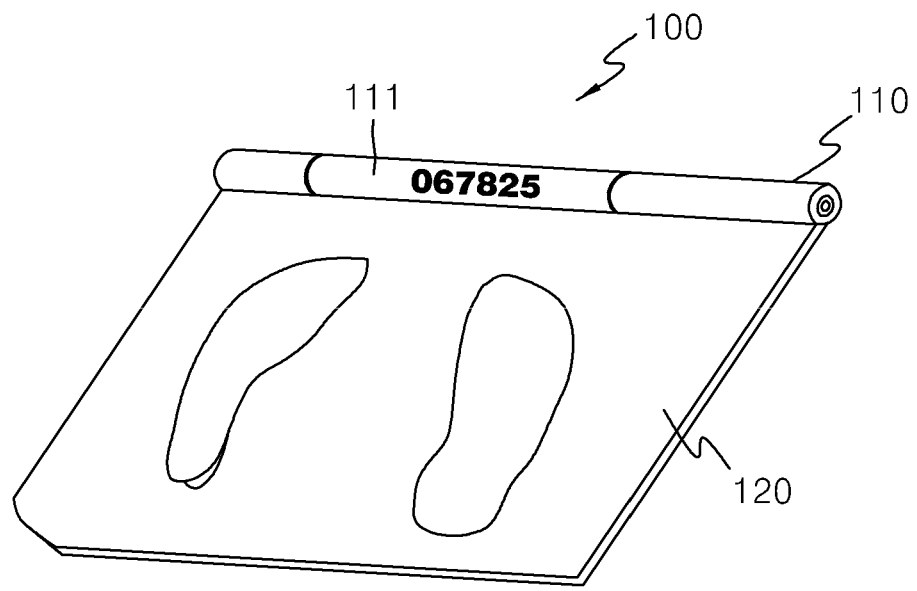

[FIG. 4]
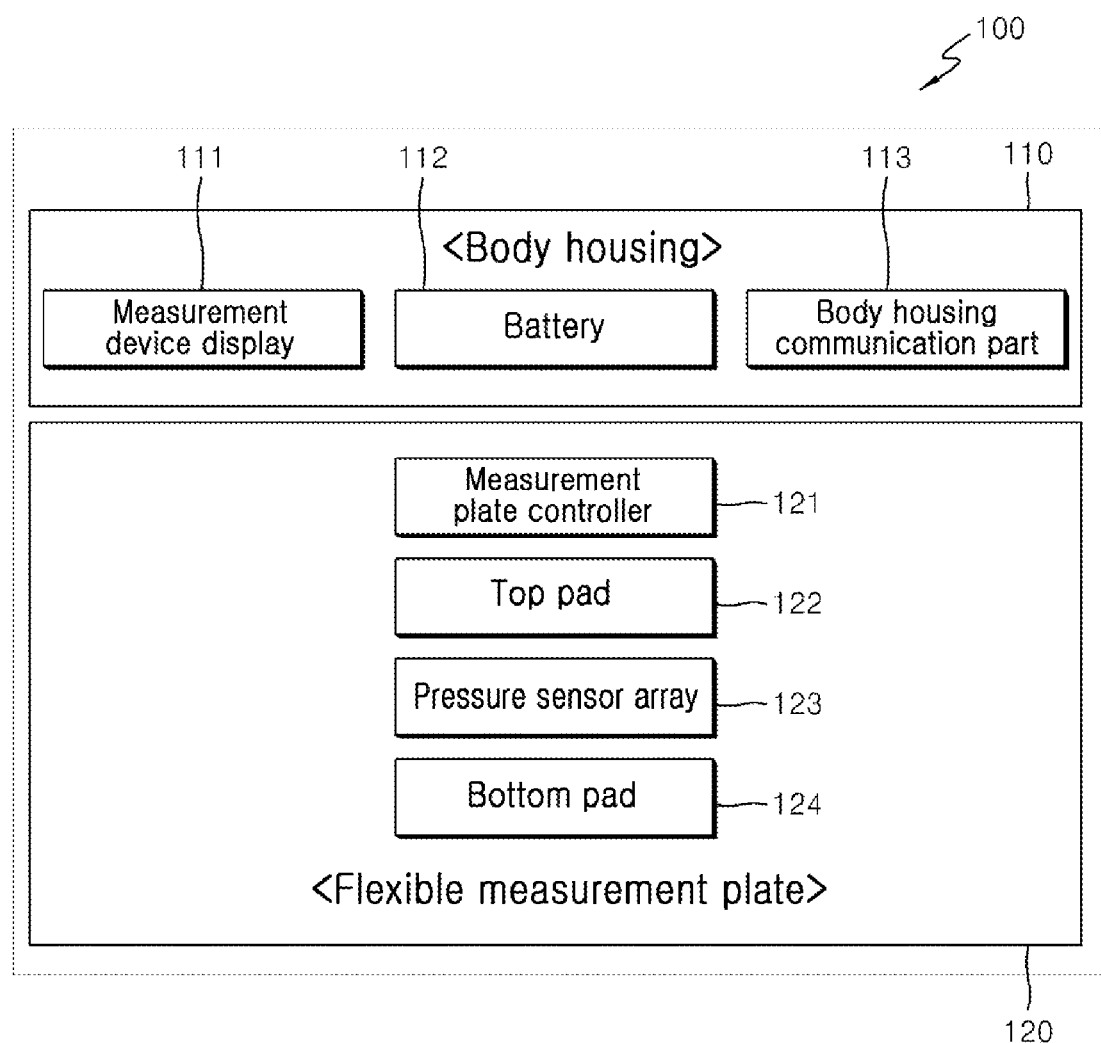

【FIG. 6】
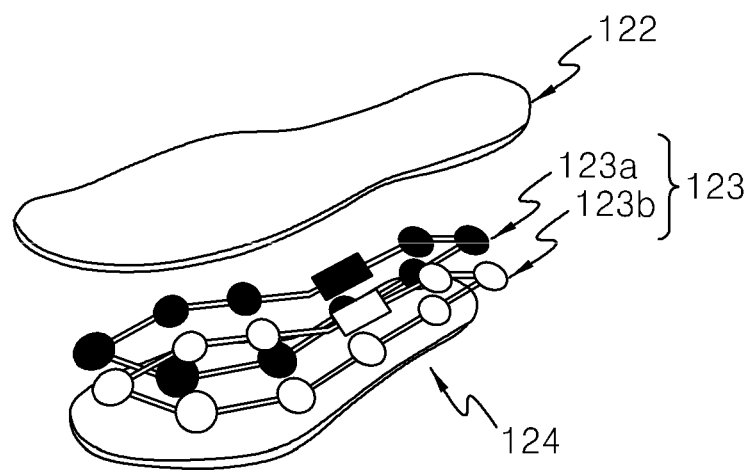
【FIG. 7】
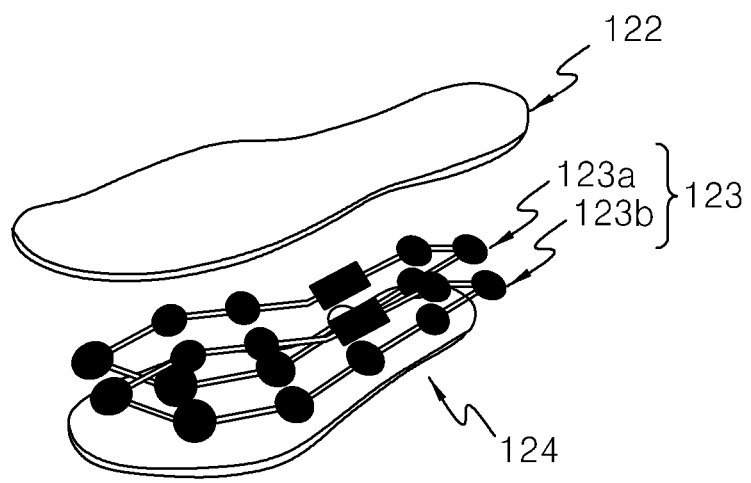

[FIG. 8]
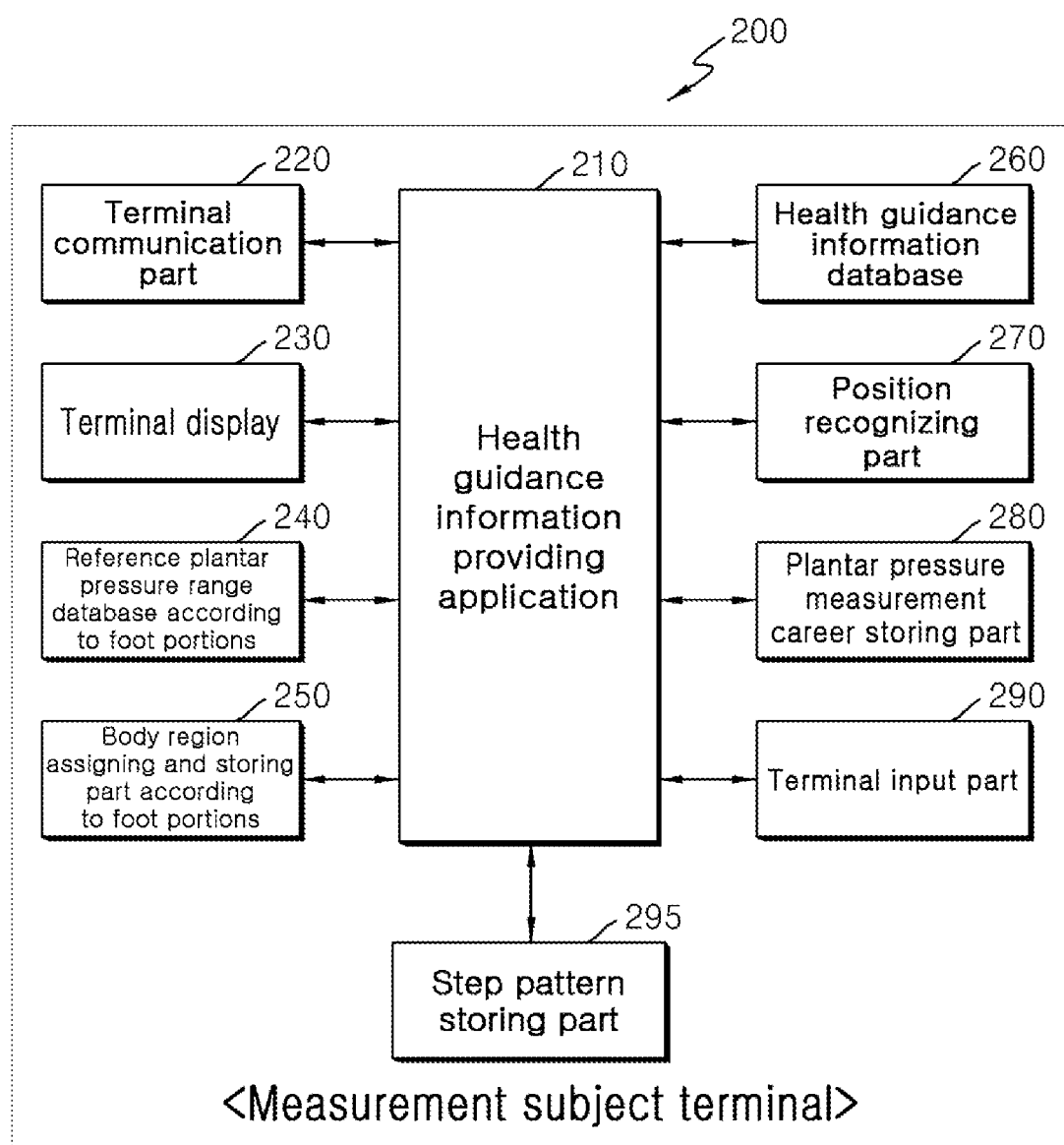

【FIG. 9】
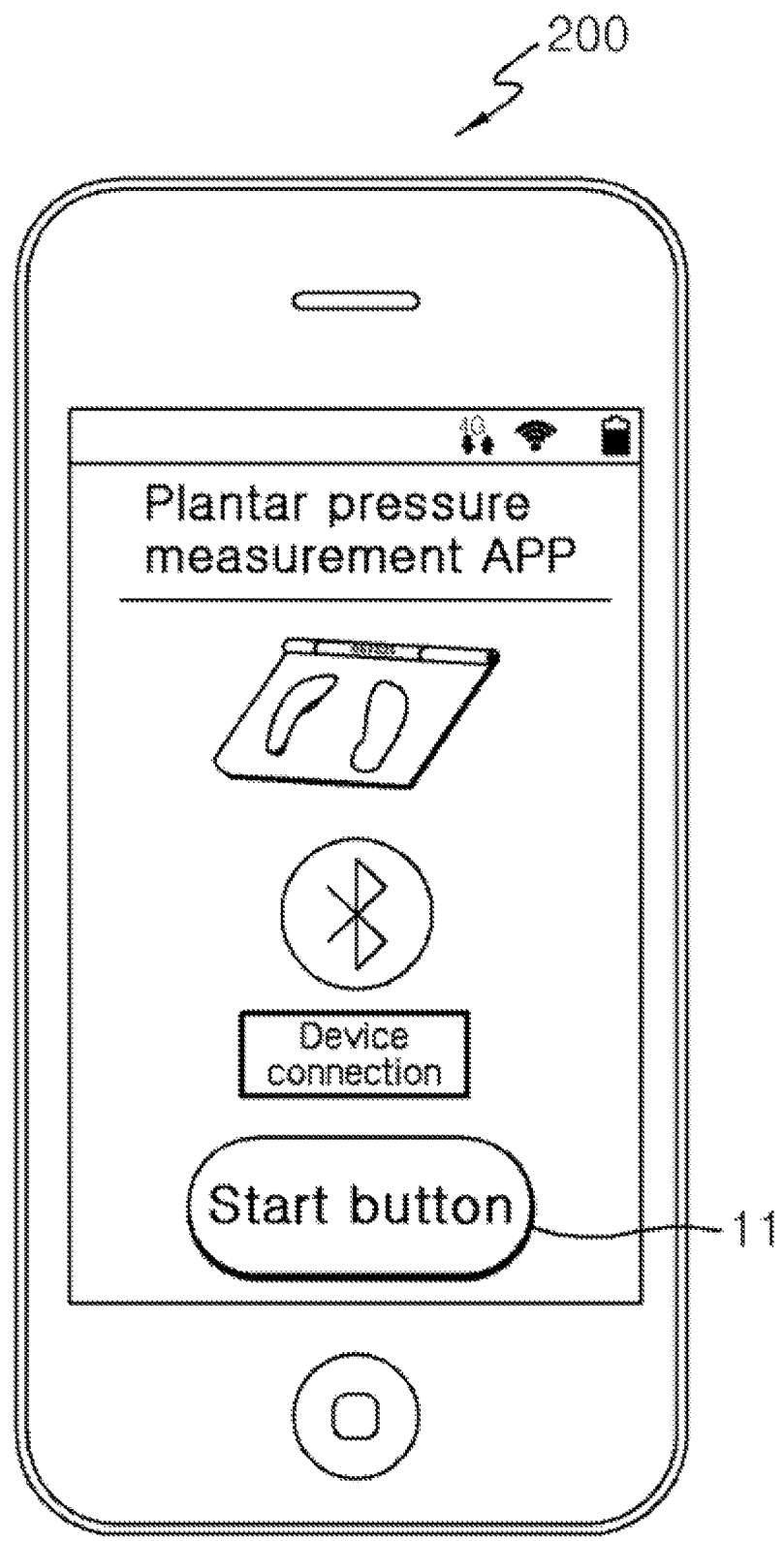

【FIG. 10】
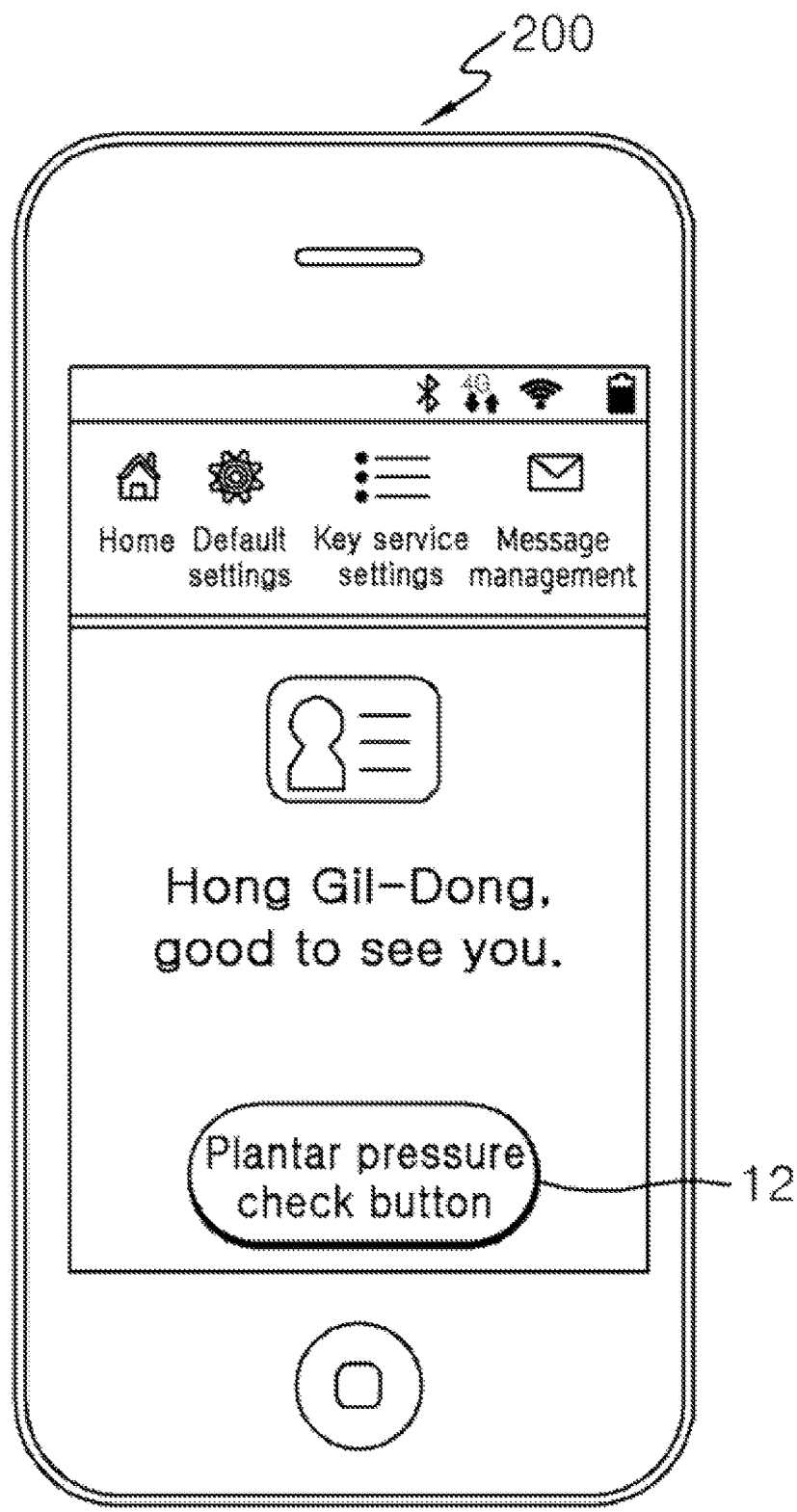

【FIG. 11】
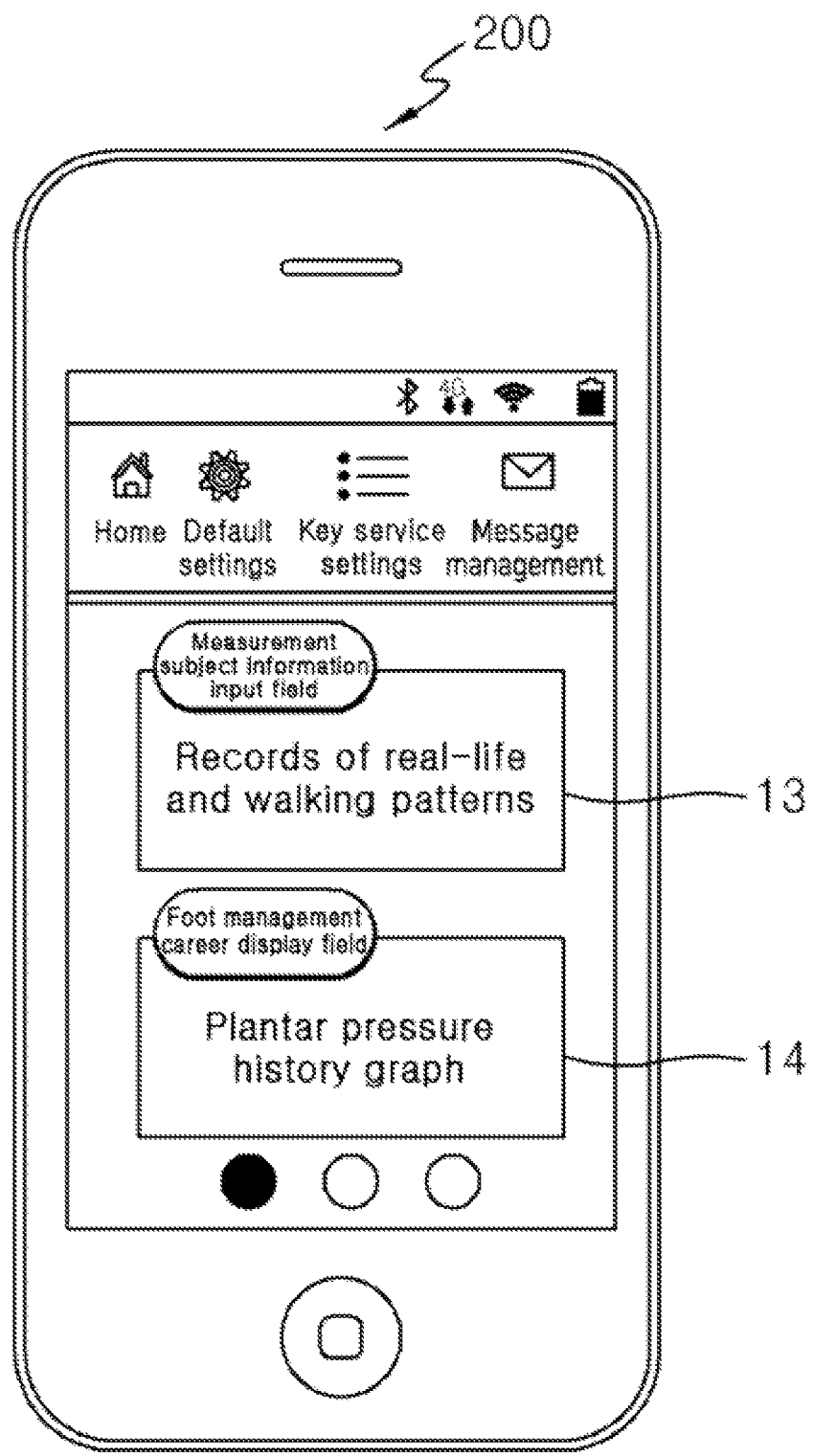

【FIG. 12】
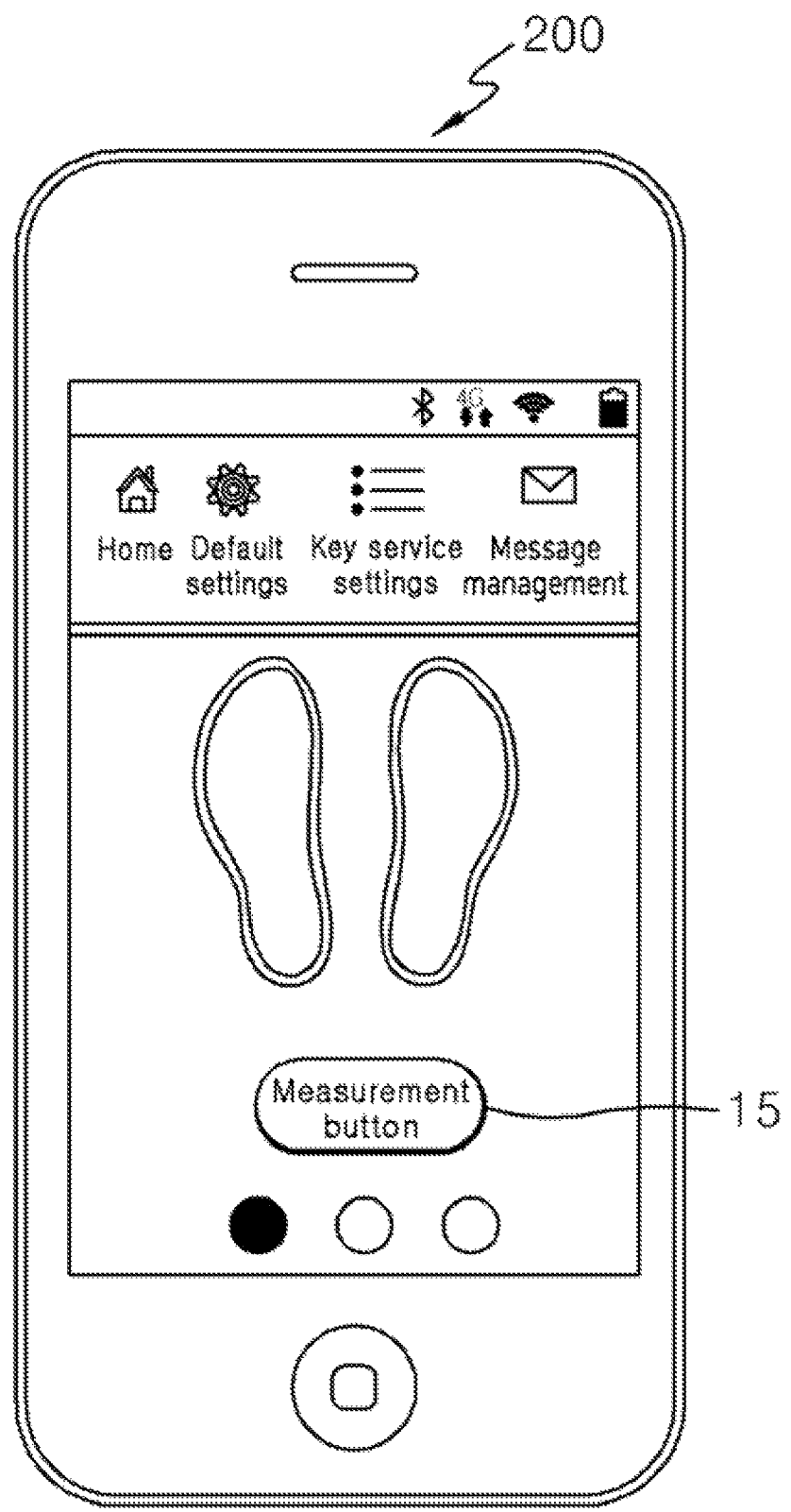

[FIG. 13]
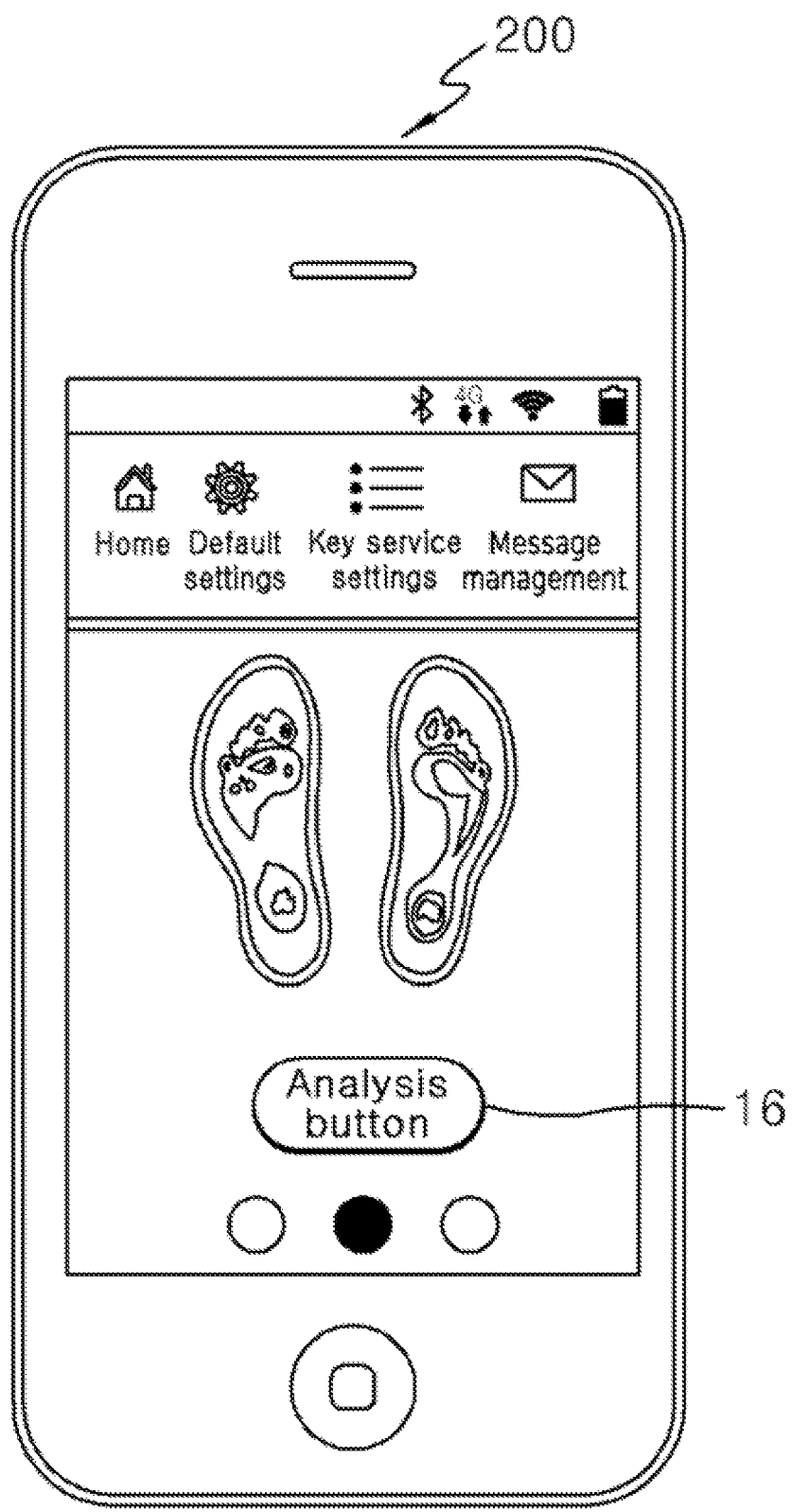

【FIG. 14】
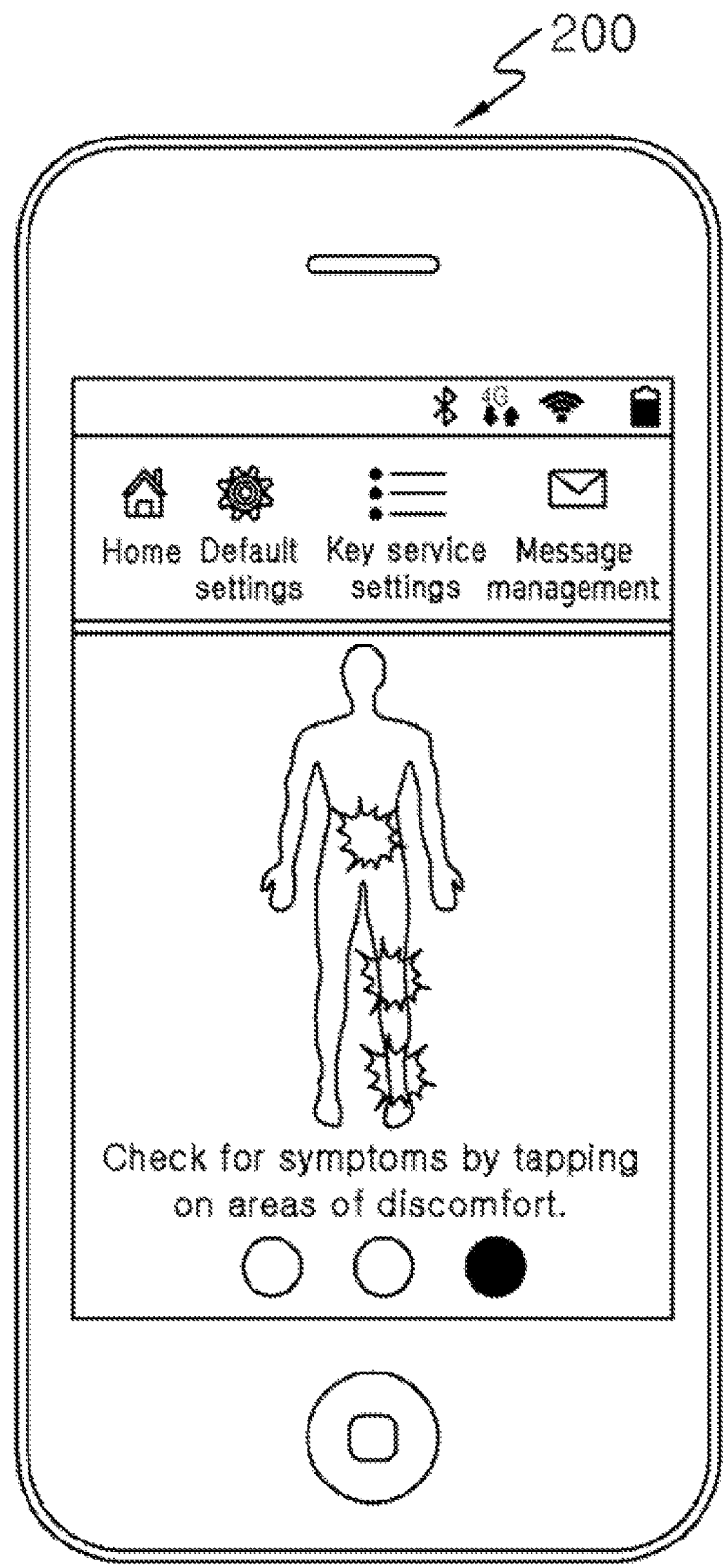

【FIG. 15】
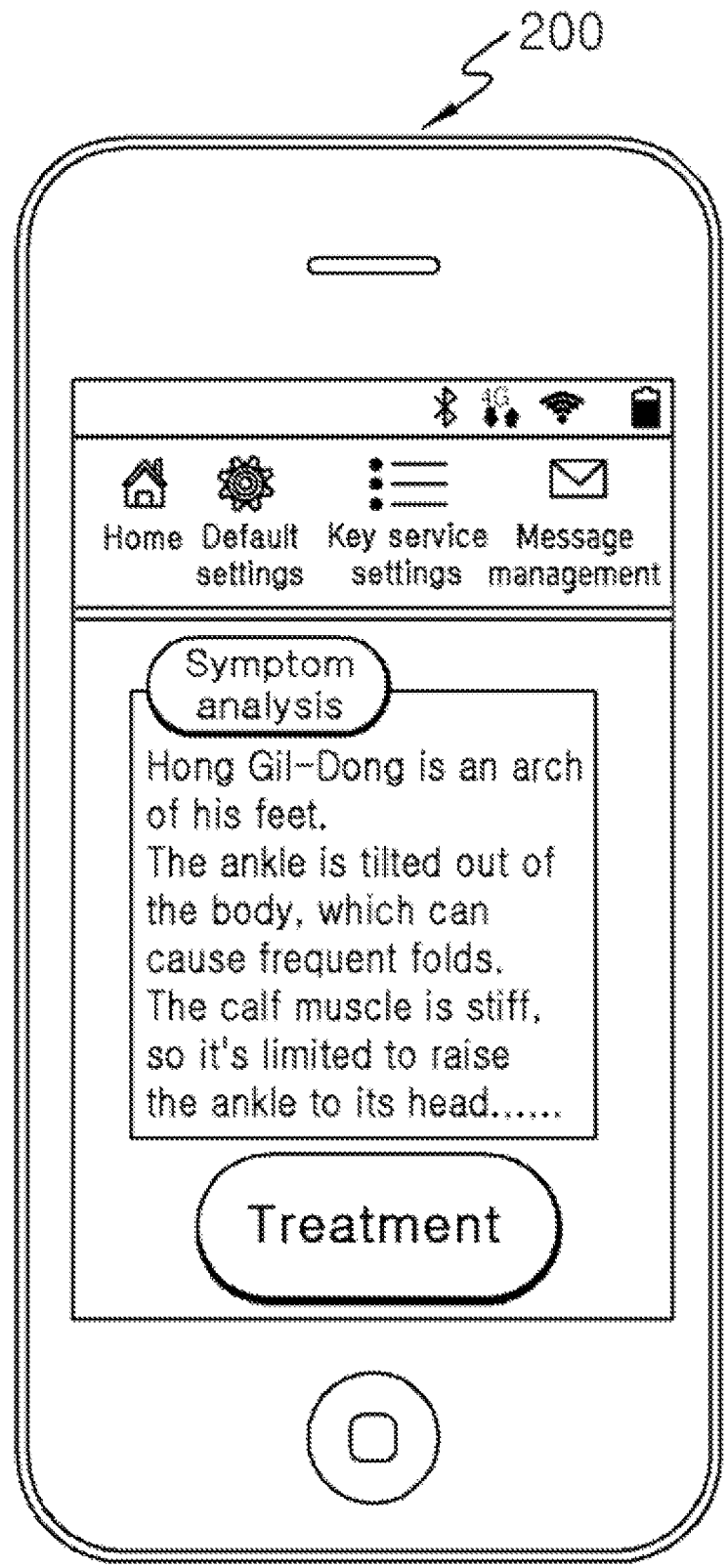

【FIG. 16】
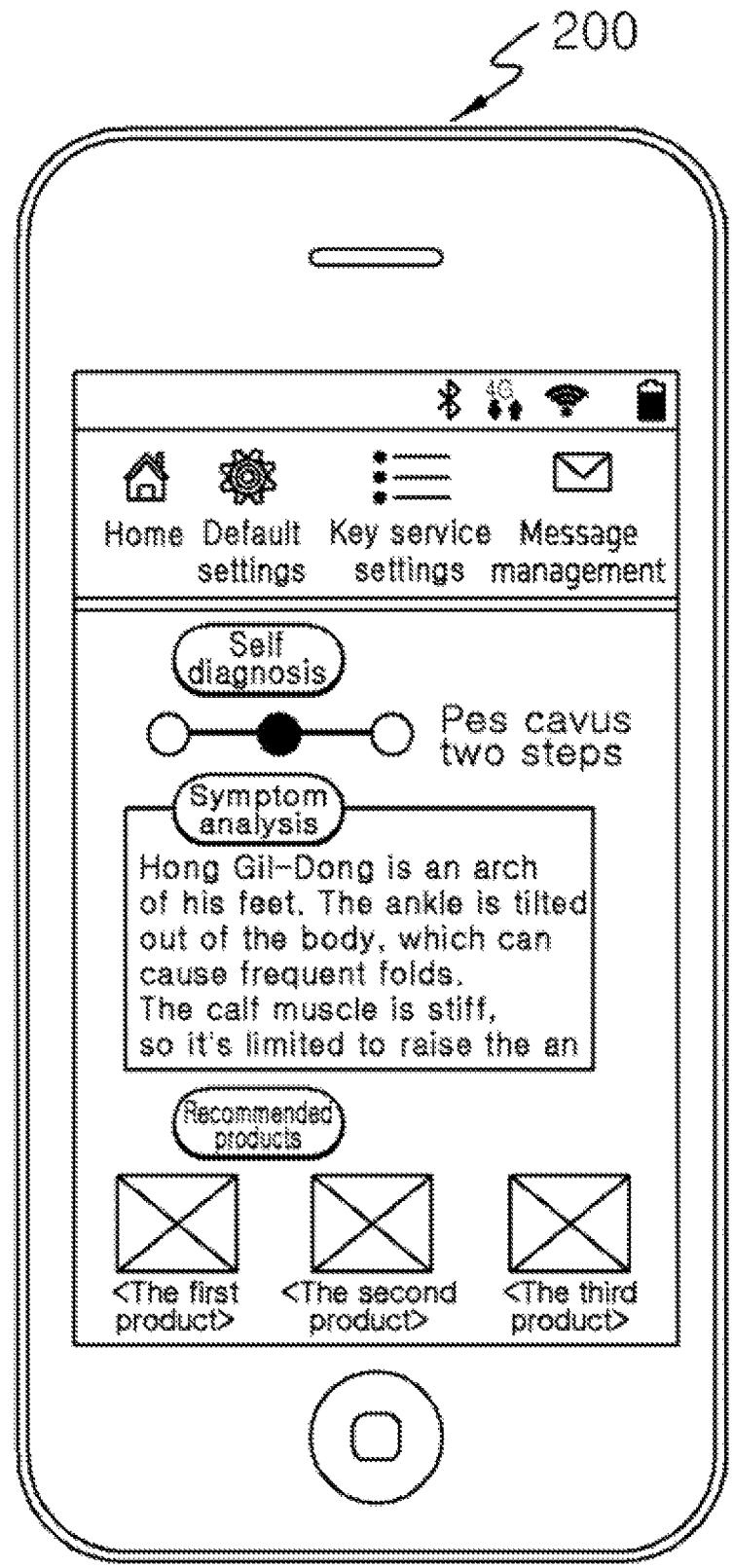

HEALTH INFORMATION PROVIDING SYSTEM THROUGH PLANTAR PRESSURE MEASUREMENT

CROSS-REFERENCE TO PRIOR APPLICATIONS

This application is a National Stage Patent Application of PCT International Patent Application No. PCT/KR2017/011135 (filed on Oct. 10, 2017) under 35 U.S.C. § 371, which claims priority to Korean Patent Application No. 10-2016-0129157 (filed on Oct. 6, 2016), which are all hereby incorporated by reference in their entirety.

BACKGROUND

The present invention relates to a health information providing system and, more particularly, to a health information providing system that is capable of providing health information through plantar pressure measurement.

Generally, the feet have functions of supporting a body weight and absorbing impacts applied thereto. A step is an operation from a state where one side heel comes into contact with the ground to a state where the other side heel comes into contact with the ground. A step width is a distance between heels of the feet at the time when soles of the feet continuously come into contact with the ground, that is, a distance between both heels of the feet upon walking. A foot angle is an angle of toes toward the outside, that is, an angle between a progressive direction line of the body and a longitudinal axis of the foot, and a foot angle of about 7° is considered as an angle in a normal range.

Plantar pressures are ones of subjects to be measured, to which many interests are given in clinical and research fields of exercise science. So as to measure the plantar pressures, a force plate, a pressure platform, and an in-shoe plantar pressure measurement device have been utilized.

Further, a podoscope using a mirror and a lamp is provided, and precision equipment using high accuracy pressure sensors is provided so that it can measure planar pressures upon standing and walking. In detail, a foot diagnosis device is suggested to measure plantar pressures. A configuration of the foot diagnosis device is disclosed in Korean Utility Model Registration No. 20-0395775.

However, most of the conventional plantar pressure measurement devices are fixed types of devices which are used in hospitals and specialized treatment centers, and also, high prices for purchasing them have to be paid. Further, analysis for plantar pressures is carried out by specialists, but according to the skill of the specialists, the analysis results may be different. Moreover, good technology or popularization for managing body balance has been not suggested. In addition, the foot diagnosis device is high in thickness so that it cannot measure plantar pressures upon natural walking and it is not easy to be moved to another place. On the basis of the plantar pressures measured through the foot diagnosis device, further, health information like a measurement subject's health state is not provided for a measurement subject, so that the foot diagnosis device becomes limited in use.

SUMMARY

Accordingly, the present invention has been made in view of the above-mentioned problems occurring in the prior art, and it is an object of the present invention to provide a health information providing system through plantar pressure measurement that is capable of providing individual health information for a measurement subject.

To accomplish the above-mentioned object, according to the present invention, there is provided a health information providing system through plantar pressure measurement, the system including: a plantar pressure measurement device rolled in such a manner as to be carried and adapted to measure a measurement subject's plantar pressures in a state of being unrolled to transmit the measured plantar pressures to a measurement subject terminal; and the measurement subject terminal adapted to compare the plantar pressures received from the plantar pressure measurement device with reference plantar pressure ranges according to foot portions pre-stored, to extract and display a body region where a disease is suspected, the body region matching the foot portion having the plantar pressure exceeding the reference plantar pressure ranges according to foot portions, and to display health guidance information including guidance information on symptoms and treatments of the extracted body region where the disease is suspected.

The plantar pressure measurement device includes: a body housing having a shape of a bar and adapted to wiredly or wirelessly transmit the measured plantar pressures to the measurement subject terminal; and a flexible measurement plate coupled to the body housing on one end thereof in such a manner as to be flexibly rolled to the external surface of the body housing, so that if the measurement subject's feet are located on the top thereof, the flexible measurement plate measures the measurement subject's plantar pressures and transmits the measured plantar pressures to the body housing.

The flexible measurement plate includes: a pressure sensor array having a plurality of pressure sensors adapted to measure the measurement subject's plantar pressures; a flexible top pad coupled to top of the pressure sensor array; a flexible bottom pad coupled to underside of the pressure sensor array; and a measurement plate controller adapted to activate the plurality of pressure sensors to measure the measurement subject's plantar pressures and to transmit the measured plantar pressures to the body housing.

The body housing includes: a measurement device display disposed on the surface thereof; a battery connected to an external charging cable, charged with power received thereto, and providing the power to the measurement device display and the plurality of pressure sensors; and a body housing communication part adapted to transmit the plantar pressures received from the flexible measurement plate to the measurement subject terminal through wired communication or wireless communication.

The measurement subject terminal includes: a terminal communication part adapted to receive the plantar pressures from the body housing communication part through wired or wireless communication; a terminal display adapted to display the health guidance information including the guidance information on symptoms and treatments of the extracted body region where the disease is suspected; a reference plantar pressure range database according to foot portions for assigning and storing the reference plantar pressure ranges according to foot portions; a body region assigning and storing part according to foot portions for assigning and storing body regions where diseases related to foot portions are suspected; a health guidance information database for assigning and storing the health guidance information including the guidance information on the symptoms and treatments of body regions where diseases are suspected; and a health guidance information providing application adapted to extract and display, if there is the foot portion having the plantar pressure exceeding the reference plantar pressure ranges according to foot portions, the body region where the disease related to the foot portion is suspected, and to display the health guidance information matching the extracted body region where the disease is suspected.

The measurement subject terminal includes: a position recognizing part adapted to recognize a position of the measurement subject terminal; and a plantar pressure measurement career storing part adapted to store a date, time, and position when the plantar pressures are received from the plantar pressure measurement device, and the health guidance information providing application displays the plantar pressure measurement career according to time on the terminal display.

The measurement subject terminal includes a terminal input part adapted to receive the measurement subject's daily life pattern from the measurement subject before the plantar pressures are measured, and the plantar pressure measurement career storing part stores the measurement subject's daily life pattern information when the measured plantar pressures exceed the reference plantar pressure ranges according to foot portions, so that the health guidance information providing application provides the plantar pressure measurement career according to time and also provides the measurement subject's daily life pattern information when the measured plantar pressures exceed the reference plantar pressure ranges according to foot portions.

The measurement subject terminal includes a step pattern storing part adapted to recognize and store step pattern information from the measurement subject before the plantar pressures are measured, and the plantar pressure measurement career storing part stores the measurement subject's step pattern information when the measured plantar pressures exceed the reference plantar pressure ranges according to foot portions, so that the health guidance information providing application provides the plantar pressure measurement career according to time and also provides the measurement subject's step pattern information when the measured plantar pressures exceed the reference plantar pressure ranges according to foot portions.

According to the present invention, the health information providing system can provide health information for body balance through the plantar pressure measurement and further provide systematic health care service for the measurement subject's real life. In addition, the health information providing system according to the present invention can provide health information for the measurement subject and allow big data related to the feet to be freely utilized by shoe, sports product, and health care product companies.

BRIEF DESCRIPTION OF THE DRAWINGS

FIG. 1 is a block diagram showing a health information providing system through plantar pressure measurement according to the present invention.

FIG. 2 is a perspective view showing a roll-type plantar pressure measurement device in the health information providing system according to the present invention.

FIG. 3 is a perspective view showing an unrolled state of the plantar pressure measurement device in the health information providing system according to the present invention.

FIG. 4 is a block diagram showing the plantar pressure measurement device in the health information providing system according to the present invention.

FIG. 6 is a sectional view showing a state where only a first pressure sensor array is activated in the health information providing system according to the present invention.

FIG. 7 is a sectional view showing a state where both of the first pressure sensor array and the second pressure sensor array are activated in the health information providing system according to the present invention.

FIG. 8 is a block diagram showing a configuration of a measurement subject terminal in the health information providing system according to the present invention.

FIGS. 9 to 16 are front views showing driving processes of the measurement subject terminal in the health information providing system according to the present invention.

DETAILED DESCRIPTION

Advantages and characteristics of the present invention will be more clearly understood from the detailed description as will be described below and the attached drawings. Before the present invention is disclosed and described, it is to be understood that the disclosed embodiments are merely exemplary of the invention, which can be embodied in various forms. Therefore, specific structural and functional details disclosed herein are not to be interpreted as limiting, but merely as a basis for the claims. If it is determined that the detailed explanation on the well known technology related to the present invention makes the scope of the present invention not clear, the explanation will be avoided for the brevity of the description.

Figure 5A:
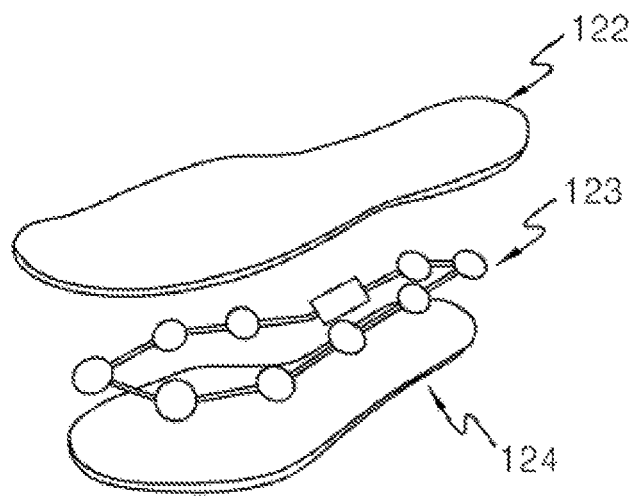
FIGS. 5A and 5B are sectional views showing a top pad, a bottom pad, and a pressure sensor array in the health information providing system according to the present invention.
Figure 5B:
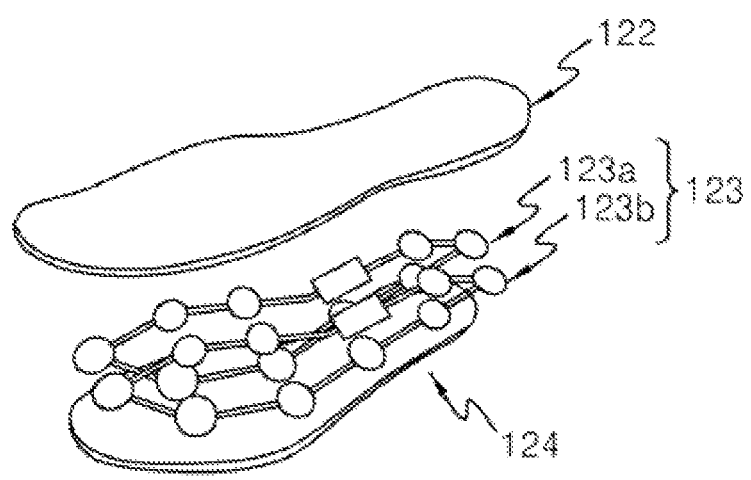

FIG. 1 is a block diagram showing a health information providing system through plantar pressure measurement according to the present invention, FIG. 2 is a perspective view showing a roll-type plantar pressure measurement device in the health information providing system according to the present invention, FIG. 3 is a perspective view showing an unrolled state of the plantar pressure measurement device in the health information providing system according to the present invention, FIG. 4 is a block diagram showing the plantar pressure measurement device in the health information providing system according to the present invention, FIGS. 5A and 5B are sectional views showing a top pad, a bottom pad, and a pressure sensor array in the health information providing system according to the present invention, FIG. 6 is a sectional view showing a state where only a first pressure sensor array is activated in the health information providing system according to the present invention, and FIG. 7 is a sectional view showing a state where both of the first pressure sensor array and the second pressure sensor array are activated in the health information providing system according to the present invention.

As shown in FIG. 1, the health information providing system through plantar pressure measurement according to the present invention includes a plantar pressure measurement device 100 and a measurement subject terminal 200.

The plantar pressure measurement device 100 serves to measure a measurement subject's plantar pressures to transmit the measured plantar pressures to the measurement subject terminal 200 wiredly or wirelessly. The plantar pressure measurement device 100 is flexible so that it can be rolled, and as shown in FIG. 2, accordingly, it is rolled and carried by the measurement subject. As shown in FIG. 3, further, if the plantar pressure measurement device 100 is unrolled to allow the measurement subject to stand thereon, it can measure the measurement subject's plantar pressures.

As shown in FIG. 4, the plantar pressure measurement device 100 includes a body housing 110 and a flexible measurement plate 120.

The body housing 110 has a shape of a bar and serves to wiredly or wirelessly transmit the measured plantar pressures to the measurement subject terminal 200. The body housing 110 includes a measurement device display 111 disposed on the surface thereof, a battery 112 connected to an external charging cable, charged with power received thereto, and providing the power to the measurement device display 111 and pressure sensors, and a body housing communication part 113 for transmitting the plantar pressures received from the flexible measurement plate 120 to the measurement subject terminal 200 through wired communication or wireless communication. In this case, the wired communication is carried out by connecting the body housing communication part 113 with the measurement subject terminal 200 through a USB cable, and the wireless communication is by connecting the body housing communication part 113 with the measurement subject terminal 200 through Bluetooth, infrared communication, and the like.

The flexible measurement plate 120 is coupled to the body housing 110 on one end thereof and is a flexible plate, as shown in FIG. 2, in such a manner as to be rolled to the external surface of the body housing 110. In a state where the flexible measurement plate 120 is unrolled, if the measurement subject's feet are located on the top of the flexible measurement plate 120, the flexible measurement plate 120 measures the measurement subject's plantar pressures and transmits the measured plantar pressures to the body housing communication part 113 of the body housing 110.

The flexible measurement plate 120 includes a measurement plate controller 121, a pressure sensor array 123, a top pad 122, and a bottom pad 124.

The measurement plate controller 121 serves to activate the pressure sensors to allow the plantar pressures of the measurement subject to be measured and then provide the measured plantar pressures to the body housing 110.

Like this, the pressure sensors for sensing the plantar pressures are provided, and referring to FIG. 5A, the pressure sensor array 123 has the pressure sensors arranged in a form of a matrix to measure the measurement subject's plantar pressures between the top pad 122 and the bottom pad 124. The top pad 122 is flexible in such a manner as to be coupled to top of the pressure sensor array 123, and the bottom pad 124 is flexible in such a manner as to be coupled to underside of the pressure sensor array 123.

Further, as shown in FIG. 5B, the pressure sensor array 123 includes a first pressure sensor array 123a and a second pressure sensor array 123b between the top pad 122 and the bottom pad 124. Accordingly, the measurement subject's plantar pressures are measured through the respective pressure sensors of the first pressure sensor array 123a and the second pressure sensor array 123b, thereby obtaining accurate measurement results.

However, it is not desirable that all of the pressure sensors of the pressure sensor array 123 should be activated to measure the measurement subject's plantar pressures. Since the plantar pressure measurement device 100 is rolled and carried by the measurement subject, it receives the driving power from the charged battery 112, and if all of the pressure sensors of the pressure sensor array 123 are activated whenever the measurement subject's plantar pressures are measured, accordingly, the power of the battery 112 becomes more rapidly consumed.

According to the present invention, as shown in FIG. 6, only the first pressure sensor array 123a is activated by the control of the measurement plate controller 121 to obtain primary measurement plantar pressures. Since the second pressure sensor array 123b is not activated, accordingly, the power of the battery 112 can be saved. Of course, the first pressure sensor array 123a activated and the second pressure sensor array 123b not activated may change into each other.

If it is checked in the primary measurement plantar pressures that the plantar pressure on a given foot portion exceeds a reference plantar pressure ranges according to foot portions, as shown in FIG. 7, both of the first pressure sensor array 123a and the second pressure sensor array 123b are activated to obtain secondary measurement plantar pressures. Accordingly, the power of the battery 112 is saved, and further, the plantar pressures can be accurately measured.

On the other hand, the measurement subject terminal 200 is the terminal used by the measurement subject whose plantar pressures are measured. For example, the measurement subject terminal 200 may be a smartphone, as shown in the drawing, and of course, it may be a desktop PC, a tablet PC, a slate PC, a laptop computer, a digital broadcasting terminal, PDA (Personal Digital Assistants), PMP (Portable Multimedia Player), and so on. Further, the terminal to which the present invention is applicable may include all of terminals with which communication can be performed, without limitation to the above-mentioned devices.

The measurement subject terminal 200 compares the plantar pressures received from the plantar pressure measurement device 100 with the reference plantar pressure ranges according to foot portions pre-stored, extracts and displays a body region where a disease is suspected, the body region matching the foot portion having the plantar pressure exceeding the reference plantar pressure ranges according to foot portions, and displays health guidance information including guidance information on symptoms and treatments of the extracted body region where the disease is suspected. Hereinafter, an explanation on the operations of the measurement subject terminal 200 will be given with reference to FIG. 8.

FIG. 8 is a block diagram showing a configuration of the measurement subject terminal in the health information providing system according to the present invention, and FIGS. 9 to 16 are front views showing driving processes of the measurement subject terminal in the health information providing system according to the present invention.

As shown in FIG. 8, the measurement subject terminal 200 includes a terminal communication part 220, a terminal display 230, a reference plantar pressure range database 240 according to foot portions, a body region assigning and storing part 250 according to foot portions, a health guidance information database 260, and a health guidance information providing application 210. Further, the measurement subject terminal 200 includes a position recognizing part 270, a plantar pressure measurement career storing part 280, a terminal input part 290, and a step pattern storing part 295.

The terminal communication part 220 receives the plantar pressures from the body housing communication part 113 of the plantar pressure measurement device 100 through wired or wireless communication. In this case, the wired communication is carried out by connecting the terminal communication part 220 with the body housing communication part 113 of the plantar pressure measurement device 100 through a USB cable or a universal serial bus, and the wireless communication is by connecting the terminal communication part 220 with the body housing communication part 113 of the plantar pressure measurement device 100 through wireless communication such as infrared radiation communication, Bluetooth, home RF (Radio Frequency), and wireless LAN.

The terminal display 230 serves to display the health guidance information including the guidance information on symptoms and treatments of the extracted body region where the disease is suspected.

The reference plantar pressure range database 240 according to foot portions is a database in which the reference plantar pressure ranges according to foot portions are assigned and stored. For example, a first reference plantar pressure range is assigned to the rearfoot, a second reference plantar pressure range to a forefoot, a third reference plantar pressure range to the midfoot, and a fourth reference plantar pressure range to an arch of the foot. If the sole of the foot is placed on a plane, at this time, the arch of the foot means an area of the foot formed through the contact of the sole of the foot with the plane.

The body region assigning and storing part 250 according to foot portions is a database in which body regions where diseases related to the foot portions are suspected are assigned and stored. For example, the forefoot is assigned to the waist, and the rearfoot to the calf.

The health guidance information database 260 is a database in which the health guidance information including the guidance information on symptoms and treatments of the body regions where the diseases are suspected.

The health guidance information providing application 210 extracts and displays, if there is the foot portion having the plantar pressure exceeding the reference plantar pressure ranges according to foot portions, the body region where the disease related to the foot portion is suspected, and displays the health guidance information matching the extracted body region where the disease is suspected.

For example, if a start button 11 is pressed after logging in, as shown in FIG. 9, measurement subject information with a measurement subject picture is displayed, as shown in FIG. 10. Next, if a plantar pressure check button 12 is pressed after the measurement subject is placed on the plantar pressure measurement device 100, as shown in FIG. 11, a measurement subject information input field 13 receives records like information on daily life and step pattern from the measurement subject, and a plantar pressure career display field 14 displays a plantar pressure career state.

If a measurement button 15 is pressed by the measurement subject, as shown in FIG. 12, the values of the plantar pressures measured by the plantar pressure measurement device 100 are received. As shown in FIG. 13, the health guidance information providing application 210 displays the plantar pressures, and if an analysis button 16 is pressed, as shown in FIG. 13, the health guidance information providing application 210 analyzes whether there is the foot portion having the plantar pressure exceeding the reference plantar pressure ranges according to foot portions. If there is the foot portion having the plantar pressure exceeding the reference plantar pressure ranges according to foot portions, as shown in FIG. 14, the health guidance information providing application 210 extracts and displays the body region where the disease related to the foot portion is suspected.

Next, as shown in FIGS. 15 and 16, the health guidance information providing application 210 extracts the health guidance information matching the extracted body region where the disease is suspected and displays the extracted health guidance information on the display. Further, advertising images of recommended products for the treatments of the diseases can be displayed on the display.

On the other hand, in the display of the plantar pressure career state through the plantar pressure career display field 14, as shown in FIG. 11, the health guidance information providing application 210 displays the plantar pressure measurement career according to time to the form of a graph, and such plantar pressure measurement career includes date, time, and position when the plantar pressures are received from the plantar pressure measurement device 100. So as to recognize the position when the plantar pressures are received, the measurement subject terminal 200 includes the position recognizing part 270 for recognizing the position of the measurement subject terminal 200. The position recognizing part 270 can recognize the position of the measurement subject terminal 200 through the reception of GPS information. Accordingly, even if the plantar pressures of the measurement subject carrying the plantar pressure measurement device 100 are measured in any place, the position at which the plantar pressures are measured is also recorded, so that the measurement subject can make his or her daily plan in the future on the basis of the position information at the time when his or her plantar pressure state is good.

On the other hand, the measurement subject information input field 13 as shown in FIG. 11 is a field for receiving the records like the information on daily life and step pattern from the measurement subject. To do this, the measurement subject terminal 200 includes the terminal input part 290 for receiving the measurement subject's daily life pattern from the measurement subject before the plantar pressure are measured. For example, the measurement subject's daily life pattern like climbing all day, working in an office all day, and so on is inputted by the measurement subject.

Further, the plantar pressure measurement career storing part 280 also stores the measurement subject's daily life pattern information when the measured plantar pressures exceed the reference plantar pressure ranges according to foot portions.

The health guidance information providing application 210 provides the plantar pressure measurement career according to time and also provides the measurement subject's daily life pattern information when the measured plantar pressures exceed the reference plantar pressure ranges according to foot portions. Accordingly, the measurement subject can recognize his or her daily life pattern at the time when the measured plantar pressures exceeding the reference plantar pressure ranges according to foot portions are determined as bad values, so that he or she tries to avoid the corresponding daily life pattern.

On the other hand, the daily life pattern is inputted received by the measurement subject, and therefore, it is inconvenient for the measurement subject to directly input the daily life pattern. So as to remove such inconveniences, the measurement subject terminal 200 further includes the step pattern storing part 295 for recognizing and storing step pattern information from the measurement subject before the plantar pressures are measured. Like a pedometer, the step pattern storing part 295 recognizes and stores steps and a step patterns, and for example, the measurement subject's step pattern in which his or her left foot is moved faster than the right foot is recognized and stored.

The plantar pressure measurement career storing part 280 also stores the measurement subject's step pattern information when the measured plantar pressures exceed the reference plantar pressure ranges according to foot portions. Also, the health guidance information providing application 210 provides the plantar pressure measurement career according to time and also provides the measurement subject's step pattern information when the measured plantar pressures exceed the reference plantar pressure ranges according to foot portions. Accordingly, the measurement subject can recognize his or her step pattern at the time when the disease related to the foot portion having the plantar pressure exceeding the reference plantar pressure ranges according to foot portions is suspected, so that he or she tries to correct his or her step pattern.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

The invention claimed is:

1. A health information providing system through plantar pressure measurement, the system comprising:
    a plantar pressure measurement device including a body housing and a flexible sensing pad attached to the body housing, and configured to measure user's plantar pressures and to transmit measured user's plantar pressures to a user terminal; and
    the user terminal including at least one micro-processor and configured
        to receive information from a user through a user interface thereof,
        to recognize and store a first step pattern of the user before the user's plantar pressures are measured,
        to compare the user's plantar pressures received from the plantar pressure measurement device with reference plantar pressure ranges according to foot portions pre-stored,
        to extract and display a body region where a disease is suspected, the body region matching a foot portion having a measured plantar pressure exceeding a reference plantar pressure range for the foot portion,
        to store a second step pattern of the user when the measured user's plantar pressures exceed the reference plantar pressure ranges according to the foot portions, and
        to display a plantar pressure measurement career according to time, the second step pattern of the user, and health guidance information including guidance information on symptoms and treatments of the body region which is extracted and where the disease is suspected,
    wherein the flexible sensing pad comprises:
        a pressure sensor array having a plurality of pressure sensors which form a first pressure sensor array and a second pressure sensor array for measuring the user's plantar pressures, and
        a controller configured to activate the plurality of pressure sensors to measure the user's plantar pressures and to transmit the measured user's plantar pressures to the body housing,
    wherein the controller is configured to activate the first pressure sensor array only first when measuring the user's plantar pressures and to active the second pressure sensor array together with the first pressure sensor array when the user's plantar pressures measured by the first pressure sensor array only exceed the reference plantar pressure ranges according to the foot portions.

2. The health information providing system according to claim 1, wherein
    the body housing has a shape of a bar and is configured to wiredly or wirelessly transmit the measured user's plantar pressures to the user terminal; and
    the flexible sensing pad is coupled to the body housing on one end thereof in such a manner as to be flexibly rolled to an external surface of the body housing, so that if the user's feet are located on a top thereof, the flexible sensing pad measures the user's plantar pressures and transmits the measured user's plantar pressures to the body housing.

3. The health information providing system according to claim 1, wherein the flexible sensing pad further comprises:
    a flexible top pad coupled to top of the pressure sensor array; and
    a flexible bottom pad coupled to underside of the pressure sensor array.

4. The health information providing system according to claim 1, wherein the body housing comprises:
    a measurement device display disposed on a surface thereof;
    a battery connected to an external charging cable, charged with power received thereto, and providing the power to the measurement device display and the flexible sensing pad; and
    transmitter configured to transmit the user's plantar pressures received from the flexible sensing pad to the user terminal through wired communication or wireless communication.

5. The health information providing system according to claim 1, wherein the user terminal comprises:
    a receiver configured to receive the user's plantar pressures transmitted from the plantar pressure measurement device through wired or wireless communication;
    a terminal display configured to display the health guidance information including the guidance information on symptoms and treatments of the extracted body region where the disease is suspected;
    a reference plantar pressure range database configured to assign and store the reference plantar pressure ranges according to the foot portions;
    a body region assigning and storing database configured to assign and store body regions related the foot portions and where diseases are suspected;
    a health guidance information database configured to assign and store the health guidance information including the guidance information on the symptoms and treatments of the body regions where diseases are suspected; and
    a health guidance information providing application software installed at the user terminal and configured to extract and display, if there is the foot portion having the measured plantar pressure exceeding the reference plantar pressure range for the foot portion, the body region related to the foot portion and where the disease is suspected, and to display the health guidance information matching the body region where the disease is suspected.

6. The health information providing system according to claim 5, wherein the user terminal comprises:
    GPS (Global Positioning System) receiver configured to receive GPS information and to recognize a position of the user terminal; and
    a plantar pressure measurement career database configured to store a date, time, and position when the measured user's plantar pressures are received from the plantar pressure measurement device, and wherein the health guidance information providing application software displays the plantar pressure measurement career according to time on the terminal display.

\* \* \* \* \*